United States Patent

Ho et al.

[11] Patent Number: 5,098,879
[45] Date of Patent: Mar. 24, 1992

[54] CATALYST FOR PREPARATION OF ORTHO-ALKYLATED PHENOLS

[75] Inventors: Ling-Wen Ho; Trong-Goang Lin; Yung-Chu Peng, all of Miaoli Hsien, Taiwan

[73] Assignee: China Technical Consultants, Inc., Taipei, Taiwan

[21] Appl. No.: 577,065

[22] Filed: Sep. 4, 1990

Related U.S. Application Data

[63] Continuation of Ser. No. 410,833, Sep. 22, 1989, abandoned.

[51] Int. Cl.⁵ .................. B01J 23/06; B01J 23/34
[52] U.S. Cl. .................. 502/324; 502/325; 502/329; 502/338; 502/343; 502/344
[58] Field of Search .......... 502/324, 325, 329, 338, 502/343, 344, 342, 330, 336

[56] References Cited

U.S. PATENT DOCUMENTS

| | | | |
|---|---|---|---|
| 3,276,894 | 10/1966 | Hund | 502/324 |
| 3,852,370 | 12/1974 | Hinkson et al. | 502/324 |
| 3,862,055 | 1/1975 | Eurlings et al. | 502/325 |
| 3,867,466 | 2/1975 | Endou et al. | 568/804 |
| 3,894,042 | 7/1975 | Tanaka et al. | 548/503 |
| 3,897,471 | 7/1975 | Herbert et al. | 502/324 |
| 3,972,836 | 8/1976 | Van Sorge | 502/324 |
| 3,974,229 | 8/1976 | Van Sorge | 502/324 |
| 4,041,085 | 8/1977 | Frabetti, Jr. | 568/747 |
| 4,546,093 | 10/1985 | Chang et al. | 502/201 |
| 4,604,375 | 8/1986 | Soled et al. | 502/324 |
| 4,629,718 | 12/1986 | Jones et al. | 502/241 |
| 4,650,781 | 3/1987 | Jones et al. | 502/324 |
| 4,791,079 | 12/1988 | Hazbun | 502/324 |
| 4,876,398 | 10/1989 | Lin et al. | 568/804 |

Primary Examiner—Anthony McFarlane
Attorney, Agent, or Firm—Bacon & Thomas

[57] ABSTRACT

The present invention provides an improved manganic oxide catalyst for the production of ortho-alkyl phenols by vapor phase reaction of a phenol having at least one ortho-hydrogen with an alcohol, the improvement comprises soaking manganic oxide in an aqueous solution of alkali metal salt, separating the soaked manganic oxide from the solution, drying and calcining the soaked manganic oxide at a temperature of 300°–600° C. for a period of 1–3 hours to form an alkali metal oxide thereon, wherein the weight ratio of the alkali metal oxide to the manganic oxide is 0.5–0.0001 wt %, preferably 0.1–0.0001 wt %.

6 Claims, No Drawings

1

CATALYST FOR PREPARATION OF ORTHO-ALKYLATED PHENOLS

This application is a continuation of application Ser. No. 07/410,833, filed Sept. 22, 1989, now abandoned.

TECHNICAL FIELD OF THE INVENTION

The present invention relates to a catalyst for preparation of ortho-alkylated phenols.

BACKGROUND OF THE INVENTION

Stephen B. Hamilton, Jr., in U.S. Pat. No. 3,446,856, first discloses a method for methylating the ortho position of phenol by the vapor phase reaction of phenol with methanol in the presence of magnesium oxide as a catalyst at a temperature ranging from 475° to 600° C., in which the service life of said catalyst at the typical reaction temperature of about 530° C. is about 90 to 100 hours, and the catalyst is pure magnesium oxide in powdered or sintered form which causes processing difficulties due to its weak mechanical properties.

Van Sorge has developed several improved catalysts for the same ortho-alkylation process as disclosed by above mentioned U.S. patent, which comprises bonding magnesium oxide with suitable materials. In his inventions of U.S. Pat. Nos. 3,843,606, 3,974,229, and 4,097,411, an inert organic polymer, manganese oxide, and silica are disclosed as a binder respectively. The bonded catalysts taught by Van Sorge, which may be molded to any desired shape, generally have the following improvements such as excellent physical properties, a service life of many hundred hours, a catalyst bed temperature varying between 460° and 500° C., and a higher degree of selectivity and yield.

Kong R. Chang and one of the inventors of present invention, Trong G. Lin in U.S. Pat. No. 4,546,093 disclosed a process for preparing 3-component catalyst system consisting of manganic oxide, ferric oxide and zinc oxide, which is used for the catalytic synthesis of 2,6-xylenol from reacting phenol with methanol. This 3-component catalyst has an improved reaction activity and selectivity with comparison to the magnesium oxide catalyst taught by Van Sorge. However, the present invention further provides a process to promote this 3-component catalyst.

In co-pending application Ser. No. 07/206,834 filed in 1988, the inventors of present invention with co-inventors disclosed a catalyst for ortho-alkylation of phenols which is prepared by calcining a co-precipitate of magnesium salt and manganese salt. Furthermore, they taught that an additional alkali metal oxide may be formed on the surface of the alkylation catalyst to enhance its service life.

SUMMARY OF THE INVENTION

The present invention provides an improved manganic oxide catalyst for the production of ortho-alkyl phenols by vapor phase reaction of a phenol having at least one ortho-hydrogen with an alcohol, the improvement comprises soaking manganic oxide in an aqueous solution of alkali metal salt, separating the soaked manganic oxide from the solution and drying, and then calcining the soaked manganic oxide at a temperature of 300°–600° C. for a period of 1–3 hours to form an alkali metal oxide thereon, wherein the weight ratio of the alkali metal oxide to the manganic oxide is 0.5–0.0001 wt %, preferably 0.1–0.0001 wt %.

Contemplated as the functional, or operative, equivalent of the manganic oxide for purpose of this invention is a mixture consisting of manganic oxide, ferric oxide and zinc oxide in which the atom ratio of Mn:Fe:Zn is from 100:20:20 to 100:0.01:0.01.

Thus, the present invention relates to an improved catalyst for the production of ortho-alkyl phenols by vapor phase reaction of a phenol having at least one ortho-hydrogen with an alcohol comprising 100 parts by weight of manganic oxide, 0–20 parts by weight of ferric oxide, and 0–20 parts by weight of zinc oxide, and said catalyst including an alkali metal oxide, wherein the weight ratio of the alkali metal oxide to the catalyst is from 0.5–0.0001.

The improved manganic oxide catalyst provided by present invention will have a significant longer service life, a higher reaction activity and selectivity with comparison to the prior art catalyst. Expecially, when the improved manganic oxide catalyst becomes deactivated over long periods of operation, it can be repeatedly regenerated and still have a comparable reaction activity and service life.

DETAILED DESCRIPTION OF THE INVENTION

The improved manganic oxide catalyst of the present invention, active for ortho-alkylation of phenols with an alcohol, is prepared by forming alkali metal oxide on the manganic oxide surface, in which the weight ratio of alkali metal oxide to manganic oxide is 0.5–0.0001 wt %, preferably 0.1–0.0001 wt %. Normally, the alkali matal oxide is deposited on the manganic oxide by impregnating the manganic oxide in an aqueous solution of alkali metal salt, separating the impregnated manganic oxide from the solution, and gradually drying the impregnated manganic oxide at an elevated temperature, and then calcining it at a temperature of 300°–600° C. for a period of 1–3 hours to form alkali metal oxide on the manganic oxide.

The above mentioned aqueous solution of alkali metal salt is prepared by dissolving soluable alkali metal salt in water. Suitable alkali metal salts are chlorides, nitrates, sulfates, acetates, oxalates and the likes.

The manganic oxide used in present invention is preferably prepared by treating an aqueous solution having solubilized manganic ions with an alkali to form a precipitate of manganic salt; filtering the treated solution with water wash to a cake of the precipitate; drying said cake and grinding into powders; molding said powders to a desired shape with an addition of water; and then calcining the molded articles at a temperature of 300°–600° C. for a period of about 1–3 hours. A surface area of at least 10 square meters per gram of manganic oxide is desirable. The shape of the manganic oxide may be in the form of Rasching rings, cylinders, tablets or any other shape known to the art.

The aqueous solution having solubilized manganic ions is prepared by dissolving soluble manganic salt in water. Examples of suitable salts are chlorides, nitrates, sulfates, acetates, oxalates and the likes.

The amount of the alkali used in the above mentioned preparation should be such as to provide a complete precipitation of solubilized manganic ions. Generally, the solubilized manganic ions will start precipitating at a pH value of the solution of about 8.0, and it will reach a value about 9.3 or up at the end of said alkali treatment. Examples of suitable alkali are aqueous solution of ammonion hydroxide, potassium hydroxide, sodium hydroxide, sodium carbonate, potassium carbonate, sodium hydrogen carbonate, potassium hydrogen carbonate and the likes.

A 3-component mixture of manganic oxide, ferric oxide and zinc oxide having an atomic ratio of Mn:Fe:Zn ranging from 100:20:20 to 100:0.01:0.01 may be used in this invention instead of manganic oxide. The preparation of this 3-component mixture is disclosed in U.S. Pat. No. 4,546,093, details thereof are incorporated by reference.

The method for forming the ortho-alkylated phenols comprises a vapor-phase reaction of an alkyl alcohol and a non-ortho-substituted phenol in the presence of the catalyst of this invention at a catalyst bed temperature of at least 300° C., and preferably at a temperature of 380° to 500° C. In general, the process is similar to the process disclosed in the above mentioned U.S. Pat. Nos. 3,446,856 and 3,974,229, the disclosure of which is incorporated herein as reference. However, the reaction temperature of the process is lower due to the higher activity of the catalyst of this invention. The alkyl alcohol used in the ortho-alkylation process is saturated alkyl alcohol, such as methanol, ethanol, propanol, cylcohexanol, and saturated alkyl alcohols having carbon atoms less than 20, preferably less than 6, and most preferably methanol. The phenol used may be represented by the formula:

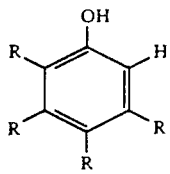

where each R is a monovalent substituent selected from the group consisting of hydrogen, alkyl, phenyl, and alkyl substituted phenyl. Mainly, methanol, phenol or o-cresol are used in the ortho-alkylation process to produce o-cresol or 2,6-dimethyl phenol product, especially 2,6-dimethyl phenol is most desired.

In order to obtain a higher yield of ortho-alkylated products, at least 1 mole of an alkyl alcohol and preferably from 1 to 4 moles of the alcohol is used for each ortho position in the phenol to be alkylated. Also, if the feed contains less than about 20 wt % of water, the catalyst will have a longer service life in the alkylation reaction.

The vapors issuing from the reactor are condensed and the products are separated in conventional manner, such as by crystallization, distillation, etc. The reaction proceeds at atmospheric pressure, but it is obvious that pressures above or below atmospheric pressure may be used. Also, the reaction can proceed in any known type of reactors, such as fixed bed reactor, fluidized bed reactor, isothermal reactor, etc.

When the catalyst becomes deactivated over long periods of operation, it can be regenerated by oxidation of the carbon deposited thereon by means of oxygen or air at flow rates such that the catalyst bed temperature does not exceed the maximum of 600° C.

The examples presented below are presented only to illustrate the invention and not meant to limit the scope of the invention. In all of the examples, precentages are by mole percents, unless otherwise indicated.

CONTROL EXAMPLE 1

Preparation of the Catalyst: (Mn2O3)

1000 g of Mn(NO3)2.6H2O was added with stirring into 1200 ml deionized water. After the added salts dissolved completely, 28 wt % ammonia water was introduced slowly until the pH value of solution reached about 9.0-9.2 to precipitate the solubilized metal ions and the mixture was kept stirring for another 0.5 hour. The mixture was filtered with deionized water wash to yield a cake of precipitate. The cake was dried at a temperature of 120° C. for 3 hours or up, and grinded into powders. The powders were mixed with water and extruded into cylindrically shaped pellets having a diameter of 4 mm and a length of 4 mm. The pellets were calcined at a temperature of 500° C. for 3 hours.

Preparation of 2,6-dimethyl phenol (2,6-DMP)

Phenol, methanol and water were mixed in a container equipped with a measuring pump, wherein the mole ratio of phenol:methanol:water was 1:6:1, and the mixture was charged into a fixed-bed isothermal reactor previously filled with 30 g catalyst made as aforementioned method at a rate of 30 ml/hour. The effluent was condensed and collected in a condenser, and then analyzed by gas chromatography. The conditions and results are summarized in run 1, Table 1.

EXAMPLE 1

The procedure of above control example 1 was repeated except that the Mn2O3 catalyst was further promoted by K2O. 100 g Mn2O3 catalyst of the control example 1 was impregnated in an aqueous solution containing 0.0021 mg of KNO3 of 30 hours, the soaked catalyst was separated and dried gradually at a temperature of 110° C., and calcined at a temperature of 500° C. for 3 hours to form a K2O layer on the catalyst. The K2O content is 0.001 wt % based on the weight of Mn2O3 catalyst. The reaction conditions and results of the ortho-alkylation process at the presence of this promoted catalyst are listed in run 1a, Table 1.

CONTROL EXAMPLE 2

Preparation of the Catalyst: (Mn/Fe/Zn Oxides)

1000 g Mn(NO3)2.6H2O, 1.4 g Fe(NO3)3.9H2O, and 1.05 g Zn(NO3)2.4H2O were added with stirring into 1200 ml deionized water. After the added salts dissolved completely, 28 wt % ammonia water was introduced slowly until the pH value of the solution reached about 9.0-9.2 to precipitate the solubilized metal ions and the mixture was kept stirring for another 0.5 hour. The mixture was filtered with deionized water wash to yield a cake of precipitate. The cake was dried at a temperature of 120° C. for 3 hours or up, and grinded into powders. The powders were mixed with water and extruded into cylindrically shaped pellets having a diameter of 4 mm and a length of 4 mm. The pellets were calcined at a temperature of 500° C. for 3 hours. The mole ratio of Mn:Fe:Zn of the calcined catalyst in this example is 100:0.1:0.1.

Preparation of 2,6-dimethyl phenol (2,6-DMP)

The procedure of preparation of 2,6-DMP in above control example 1 was repeated. The reaction conditions and results are listed in run 2, Table 1.

EXAMPLE 2

The procedure of above control example 2 was repeated except that the catalyst was further promoted by K2O. 100 g Mn/Fe/Zn oxides catalyst of the control example 2 was soaked in an aqueous solution containing 0.0021 mg of KNO3 for 30 hours, the soaked catalyst was separated and dried gradually at a temperature of 110° C., and calcined at a temperature of 500° C. for 3 hours to form a K2O layer on the catalyst. The K2O content is 0.001 wt % based on the weight of Mn/Fe/Zn oxides catalyst. The reaction conditions and results of the ortho-alkylation process at the presence of this promoted catalyst are listed in run 2a, Table 1.

EXAMPLE 3

The object of this example is to illustrate that the Mn2O3 catalysts can be promoted by depositing different alkali metal oxides on their surface. The procedure of above example 1 was repeated with the substitution of different alkali metal salts. The conditions and results are listed in run 3 and 4 of Table 1, respectively.

TABLE 1

| | | Reaction pressure 9 kg/cm2, WHSV$^{(i)}$ = 0.9 hr$^{-1}$ | | | | Service life$^{(iv)}$ |
|---|---|---|---|---|---|---|
| | | Initial | Initial conversion$^{(ii)}$ | Initial selectivity$^{(iii)}$ | | |
| Run | Catalyst | temp. (°C.) | of phenol (%) | 2,6-DMP | 2,4,6-TMP | (hrs) |
| 1 | Mn2O3 | 420 | 99.74 | 85.99 | 4.36 | 697.5 |
| 1a | Mn2O3 + 0.001 wt % K2O | 440 | 100.0 | 92.68 | 5.05 | 914.0 |
| 2 | Mn/Fe/Zn oxides | 420 | 100.0 | 86.40 | 7.10 | 508.0 |
| 2a | Mn/Fe/Zn oxides + 0.001 wt % K2O | 420 | 99.76 | 89.36 | 7.68 | 724.0 |
| 3 | Mn2O3 + 0.02 wt % Cs2O | 450 | 99.88 | 98.19 | 0.53 | 820.0 |
| 4 | Mn2O3 + 0.05 wt % Li2O | 460 | 100.0 | 93.12 | 4.75 | — |

$^{(i)}$WHSV is the liquid hourly space velocity and defines the weight of liquid per weight of catalyst per hour.
$^{(ii)}$The conversion of phenol = [(moles of phenol reacted)/(moles of phenol in the feed)] * 100%
$^{(iii)}$The selectivity is defined as the mole percents of 2,6-dimethyl phenol (2,6-DMP) or 2,4,6-trimethyl phenol (2,4,6-TMP) based on the total moles of alkylated phenols
$^{(iv)}$The service life is defined as the time during which the production rate of 2,6-DMP is kept above 70% from the reaction start to a reaction temperature of 480 C.

As it is shown in Table 1 that the catalysts promoted forming a layer of alkali metal oxides thereon have higher yield 2,6-DMP and prolonged service life.

EXAMPLE 4

The object of this example is to demonstrate that when the improved catalyst of present invention becomes deactivated after long periods operation, the spent catalyst can be regenerated by introducing air through the catalyst bed and still have a comparable activity, selectivity, and service life.

The deactivated catalysts of above control example 1 and example 1 were regenerated by introducing air through the catalyst bed with a controlled temperature gradually arising from about 250° C. to 500° C., respectively. The same regeneration procedure was repeated when the catalysts had become deactivated after long periods operation in the preparation of 2,6-DMP. The conditions and results are summarized in the following Table 2.

TABLE 2

| | (reaction pressure 9.00 kg/cm$^2$) | | | |
|---|---|---|---|---|
| Catalyst | No. of regeneration | Reaction Temp. (°C.) | Service life (hrs) | WHSV (hr$^{-1}$) |
| Mn2O3 | 0 | 420–480 | 191.0 | 2.40 |
| Mn2O3 | 1 | 420–480 | 119.0 | 2.40 |
| Mn2O3 | 2 | 430–480 | 119.0 | 2.40 |
| Mn2O3 | 3 | 420–480 | 102.0 | 2.40 |
| Mn2O3/K2O | 0 | 440–480 | 913.0 | 0.90 |
| Mn2O3/K2O | 1 | 420–480 | 820.0 | 0.90 |
| Mn2O3/K2O | 2 | 430–460 | 860.0 | 0.90 |
| Mn2O3/K2O | 3 | 430–470 | 1200.0 | 0.90 |
| Mn2O3/K2O | 4 | 430–470 | 1320.0 | 0.90 |

What we claim is:

1. An improved catalyst for the production of ortho-alkyl phenols by vapor phase reaction of a phenol having at least one ortho-hydrogen with an alcohol, wherein the improvement comprises a catalyst comprising a mixture of manganic oxide, ferric oxide and zinc oxide in which the atom ratio of Mn:Fe:Zn is from 100:20:20 to 100:0.01:0.01 and including an alkali metal oxide, wherein the weight ratio of the alkali oxide to the manganic oxide is from 0.5–0.0001.

2. A catalyst as claimed in claim 1, wherein the weight ratio of the alkali metal oxide to the manganic oxide is 0.1–0.0001.

3. A catalyst according to claim 2 wherein the alkali metal is potassium, cesium or lithium.

4. A catalyst according to claim 3 wherein the alkali metal is potassium.

5. A catalyst according to claim 1 which has a surface area of at least 10 m$^2$/g of manganic oxide.

6. An improved catalyst for the production of ortho-alkyl phenols by vapor phase reaction of a phenol having at least one ortho-hydrogen with an alcohol, wherein the improvement comprises a catalyst comprising a mixture of manganic oxide, ferric oxide and zinc oxide in which the atom ratio of Mn:Fe:Zn is from 100:20:20 to 100:0.01:0.01, wherein the catalyst is first impregnated in an aqueous solution of an alkali metal salt, separating the impregnated catalyst from the solution, drying the impregnated catalyst, and calcining the impregnated catalyst at a temperature of 300°–600° C. for a period of 1–3 hours to form an alkali metal oxide thereon, wherein the weight ratio of the alkali metal oxide to the manganic oxide is 0.1–0.0001.

* * * * *